United States Patent
Yang et al.

(10) Patent No.: US 9,167,841 B2
(45) Date of Patent: Oct. 27, 2015

(54) TANGERINE PEEL EXTRACT AND ITS PREPARATION AND APPLICATION

(75) Inventors: Yiting Yang, Guangdong (CN); Hujie Luo, Guangdong (CN); Wei Sun, Guangdong (CN); Haiyan Ou, Guangdong (CN); Shuo Liu, Guangdong (CN); Chungwah Ma, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 467 days.

(21) Appl. No.: 13/355,528

(22) Filed: Jan. 21, 2012

(65) Prior Publication Data

US 2012/0189731 A1 Jul. 26, 2012

(30) Foreign Application Priority Data

Jan. 21, 2011 (CN) .......................... 2011 1 0023459

(51) Int. Cl.
*A61K 36/752* (2006.01)
*A23L 1/30* (2006.01)
*A23L 1/212* (2006.01)

(52) U.S. Cl.
CPC ............. *A23L 1/3002* (2013.01); *A23L 1/2126* (2013.01); *A61K 2236/37* (2013.01)

(58) Field of Classification Search
CPC .... A61K 2300/00; A61K 36/752; A61K 8/97
See application file for complete search history.

(56) References Cited

PUBLICATIONS

Website document entitled Tangerine Peel (Citrus reticulata) posted Mar. 13, 2005. (Available at http://www.tillotsoninstitute.com/important-herbs/tangerine-peel-citrus-reticulata.html?printerFriendly=true).*
Website document entitled "Mandarin Orange" (Available at http://freewebs.com/jumblebox/healthF?oren.html).*
Reverchon (1997) J. Supercritical Fluids 10: pp. 1-37.*
Danielski Dissertation (2007) Extraction and Fractionation of Natural Organic Compounds from Plant Materials with Supercritical Carbon Dioxide. p. 1-176.*
Revilla et al. (1998) J. Agric. Food Chem. 46: 4592-4597.*

* cited by examiner

*Primary Examiner* — Chris R Tate
*Assistant Examiner* — Russell Fiebig
(74) *Attorney, Agent, or Firm* — George G. Wang; Bei & Ocean

(57) ABSTRACT

This invention disclosed is a tangerine peel extract with the effect of weight gain. This extract uses tangerine peel as the raw ingredient and is obtained through extraction processes using supercritical $CO_2$, water, or organic solvents. The resulting extraction component contains a large quantity of flavonoids and terpenoids, which can effectively regulate the function of the spleen and stomach leading to desired weight gain. This invention also declares the preparation methods of the above mentioned tangerine peel extraction, which is simple in technique and highly effective in extraction. This invention also further declares the application of the above mentioned tangerine peel extraction in preparing healthcare food with the function of gaining weight.

3 Claims, No Drawings

TANGERINE PEEL EXTRACT AND ITS PREPARATION AND APPLICATION

FIELD OF THE INVENTION

The present invention relates to the technical field of healthcare food. In particular, it relates to the preparation and application of tangerine peel extract.

BACKGROUND OF THE INVENTION

There are reportedly 60 million people in China trying to increase body weight. According to the theory of Traditional Chinese Medicine, "the spleen is responsible for the Cangkang meridian and stomach is responsible for the cereal meridian." Emaciation of the body is mainly caused by congenital or acquired hypo-functions of the spleen and stomach as well as by deficiencies in nutrient transformation. The spleen and stomach are fundamental organs that support the performance of the body and represent sources of "Qi" and "Blood". When the spleen and stomach are healthy, the "Qi" is vigorous and "Blood" transportation and transformation are functioning at normal levels; muscles and body fat are well maintained and the limbs are strong and powerful. Otherwise, emaciation of the body and weakened limbs result. Therefore, maintaining the spleen and stomach functions and enhancing transformation and assimilation of the nutrient substances are important measures to effectively increase body weight.

The theory of Traditional Chinese Medicine emphasizes preventive measures against illness and pays attention to the therapeutic role of a well-balanced diet. The present invention is based on active substances extracted from raw materials used in traditional medicine for enhancing functions of the spleen and stomach.

SUMMARY OF THE INVENTION

The first objective of this invention is to extract the component of tangerine peel which contains an abundance of flavonoid and terpenoid compounds. Such compounds can effectively regulate the functions of the spleen and stomach, hence allowing for increased body weight.

The second objective of this invention is to offer a novel method of preparing the above-mentioned tangerine peel extract that is at once simple and highly efficient in obtaining the active compounds.

The third objective of this invention is to indicate potential healthcare benefits of the above mentioned tangerine peel extract.

The first objective of this invention is realized through the following technical scheme: the active compounds are extracted using tangerine peels as the raw material by a method that employs supercritical $CO_2$, water, or an organic solvent.

The second objective of this invention is realized through the following technical scheme: the preparation method of the above mentioned tangerine peel extract is through taking the tangerine peel as the raw material, preparing and obtaining the tangerine peel extraction via supercritical $CO_2$ extraction, water extraction or organic solvent extraction.

Using supercritical $CO_2$ extraction, the parameters of extraction are as follows: the pressure is adjusted to 10-40 MPa and the temperature set at 30-50° C. Extraction time is 1-3 hours and the $CO_2$ flow rate is 1-100 L/h. The tangerine peel extraction is thus obtained.

If water extraction is conducted, the following parameters are used: a mass ratio of tangerine peel to water of 1:5-15 and an extraction temperature of 70-100° C. The extraction is repeated 1-3 times with a single duration time lasting 1-3 hours.

If the organic solvent extraction method is used, the mass ratio of tangerine peel to organic solvent is optimal at 1:5-15 and the extraction temperature should be set at 55-80° C. The extraction is repeated 1-3 times with each extraction lasting 1-3 hours.

The preferred organic solvent for this extraction is ethanol or methanol.

The optimal size of the dried tangerine peel pieces (after pulverization) is 10-80 mesh and the resultant extract is then concentrated and dried. The concentration procedure is preferably performed under vacuum and the drying step using a frozen drying process.

The third purpose of this invention is realized through realization of the effects of the above mentioned tangerine peel extract as an active ingredient in healthcare products targeted for weight gain. Weight gain has been observed after orally taking the following: 1) the tangerine peel extract extracted with supercritical $CO_2$ and mixed with supplementary ingredients such as the glycerin and carboxymethyl cellulose; 2) the tangerine peel extract extracted with water and mixed with supplementary materials such as water; or 3) the tangerine peel extract extracted with the ethanol or methanol and combined with supplementary materials such as the water and carboxymethyl cellulose. Alternatively, tangerine peel extract may be used as the main ingredient and added with the pharmaceutically acceptable supplementary ingredients to make it into a healthcare product. Pharmaceutically acceptable supplementary material includes one or more members selected from the group consisting of mannitol, sorbitol, sodium metabisulfite, sodium hydrogensulfite, vitamin C, EDTA disodium, sodium bicarbonate, calcium bicarbonate, calcium sulfate, sodium chloride, sodium lactate, xylitol, maltose, fructose, dextran, ferrous sulphate, starch, dextrin, cane sugar, lactose, silicon derivatives, cellulose and its derivatives, carboxymethyl cellulose, gelatin, agar, Polyethylene imidacloprid ketone, glycerin, paraffin, tween-80, polyethylene glycol, compressible starch, surfactant, cyclodextrin and its derivatives, talcum powder and magnesium stearate. The resultant healthcare product can be in the dosage form of capsule, oral solution, granular formulation, pill, etc.

This invention has the following advantages:

1. The extract can both serve as food and as medicine, because it contains a large quantity of flavonoids and terpenoids, which can effectively, regulate the function of the spleen and stomach and has the efficacy of promoting digestion, hence promoting weight gain.

2. The tangerine peel extract prepared by the extraction technique of the present invention sufficiently retains and enriches the efficacy components, which functions in boosting the spleen and benefiting the stomach, accomplishing the effect of gaining weight through means such as lowering the intestine's propulsion rate, strengthening the secreting function of gastrin and inhibiting the secreting function of the motilin, etc.

The following further describes the invention through the specific embodiments and the pharmacodynamic testing data.

DETAILED DESCRIPTION OF PARTICULAR EMBODIMENTS OF THE INVENTION

The following provides some examples of the specific implementing method to describe the invention. It should be pointed out that the following specific implementing examples are only used for further explaining the invention and not for limiting the scope of the invention. Non-essential modifications and adjustments made by people of ordinary skill in the art within the spirit of the present invention are still within the scope of the invention.

Part I

The Tangerine Peel Extract and Preparation Method Thereof

Example 1

In this example, the tangerine peel extract is prepared and obtained through the following process: grind 200 g of tangerine peel into 80 mesh, place grounds into the extraction facilities of supercritical $CO_2$ using extraction pressure of 35 MPa. Use an extraction temperature of 50° C., extraction time of one hour, and flow rate of $CO_2$ is 80 L/h. Place resulting extraction into a separation tank to obtain the final extract.

Example 2

In this example, the tangerine peel extract is prepared and obtained through the following process: grind 100 g of tangerine peel into 50 mesh, place grounds into the extraction facilities of supercritical $CO_2$ using extraction pressure of 25 MPa. Use an extraction temperature of 40° C., extraction time of 2 hours, and flow rate of $CO_2$ is 20 L/h. Place resulting extraction into a separation tank to obtain the final extract.

Example 3

In this example, the tangerine peel extract is prepared and obtained through the following process: grind 20 g of tangerine peel into 10 mesh, place grounds into the extraction facilities of supercritical $CO_2$ using extraction pressure of 15 MPa. Use an extraction temperature of 30° C., extraction time of 3 hours, and flow rate of $CO_2$ is 50 L/h. Place resulting extraction into a separation tank to obtain the final extract.

Example 4

In this example, the tangerine peel extract is prepared and obtained through the following process: grind 200 g of tangerine peel into 10 mesh, add 1,000 g of water and use an extraction temperature is 90° C. Extraction lasts one hour and is repeated 2 more times, after which all the extracted liquids are combined. The final extract is obtained after the combined liquid is subjected to the processes of low pressure evaporation (the pressure is 0.08 MPa and the temperature is 50° C.), vacuum freeze and drying (under 10 Pa and at −18° C.).

Example 5

In this example, the tangerine peel extract is prepared and obtained through the following process: grind 100 g of tangerine peel into 50 mesh, add 1,000 g of water and use an extraction temperature of 100° C. The extraction lasts 2 hours and is repeated once. The two extract liquids are combined. The final extract is obtained after the combined extract liquid being subject to the processes of low pressure evaporation (the pressure is 0.08 MPa and the temperature is 50° C.), vacuum freeze and drying (under 10 Pa and at −18° C.).

Example 6

In this example, the tangerine peel extract is prepared and obtained through the following process: grind 10 g of tangerine peel into 80 mesh, add 150 g of water and use an extraction temperature of 70° C. The extraction lasts 3 hours and is repeated once. The extract liquids are combined. The final extract is obtained after the combined extract liquid being subject to the processes of low pressure evaporation (the pressure is 0.08 MPa and the temperature is 50° C.), vacuum freeze and drying (under 10 Pa and at −18° C.).

Example 7

In this example, the tangerine peel extract is prepared and obtained through the following process: grind 200 g of tangerine peel into 10 mesh, add 1,000 g of 95% (by volume) ethanol. The extraction temperature is 70° C. The extraction lasts one hour and is repeated two more times. The three extraction liquids are combined. The final extract is obtained after the combined extract liquid being subject to the processes of low pressure evaporation (the pressure is 0.08 MPa and the temperature is 45° C.), vacuum freeze and drying (under 10 Pa and at −18° C.).

Example 8

In this example, the tangerine peel extract is prepared and obtained through the following process: grind 100 g of tangerine peel into 50 mesh, add 1,000 g of 95% (by volume) ethanol. The extraction temperature is 78° C. The extraction lasts 2 hour and is repeated once. The two extraction liquids are combined. The final extract is obtained after the combined extract liquid being subject to the processes of low pressure evaporation (the pressure is 0.08 MPa and the temperature is 45° C.), vacuum freeze and drying (under 10 Pa and at −18° C.).

Example 9

In this example, the tangerine peel extract is prepared and obtained through the following process: take 20 g of tangerine peel, grind it into 80 mesh, add it into 300 g of methanol, the extraction temperature is 65° C. The extraction lasts three hours and is repeated once. The final extract is obtained after the combined extract liquid being subject to the processes of low pressure evaporation (the pressure is 0.08 MPa and the temperature is 45° C.), vacuum freeze and drying (under 10 Pa and at −18° C.).

Example 10

The tangerine peel extract prepared with supercritical $CO_2$, as in example 2, may be properly supplemented as necessary with the glycerin and carboxymethyl cellulose to make a liquid product. Alternatively, it may be combined with the other conventional supplementary materials as necessary to produce capsules, oral solutions, etc, which can be administered once per day (10 g per day).

Example 11

The tangerine peel extract extracted by water, as in example 5, may be supplemented with water according to taste or with other conventional solvents to be made into the liquid products or tablets and particles, etc. whose usage should be measured according to the human body medicine generating dose and 10 g per day, once a day.

Example 12

The tangerine peel extraction prepared by ethanol as in example 8, adjusted according to taste, should be properly supplemented with water, carboxymethyl cellulose or other conventional solvents or supplementary materials to be made into the liquid products or tablets and particles, etc. whose usage is measured by the human body medicine generating dose, 10 g per day and once a day.

Part II

Test of the Tangerine Peel Extract on the Efficacy of Weight Gaining

1. Testing Institution

Testing Center of Hubei University of Traditional Chinese Medicine.

2. Objective of the Test

Study the effect of gaining weight of the tangerine peel extract of the present invention.

3. Material, Grouping and Dosage 3.1 Testing Material:

(1) Testing Verification of the Efficacy of Gaining Weight.

Using the obtained products of the above mentioned examples 10, 11, and 12, the applicant has carried out the verification testing of the efficacy of gaining weight, and measured by the human body medicine generating dose, 10 g per day and once a day.

(2) Testing animals: female Kunming Brand little mice, weighted 18~22 g, provided by the Testing Animal Center of Tongji Medical College.

(3) Main Equipment and Reagents of the Test.

I. Nissan Olympus Automatic Biochemistry Analyzer;

II. Nissan KUBOTA KR-20000T Low Temperature Highspeed Centrifuge;

III. Gastrin kit, provided by Beijing Huaying Biotechnology Research Institute;

IV. IL-2 kit, provided by Wuhan Bolster Products Co., Ltd.;

V. Motilin kit, provided by Beijing Dongya Biotechnology Research Institute;

VI. BH5100 type Atom Absorption Spectroscopy: manufactured by Beijing Bohui Innovation Technology Co., Ltd.;

VII. TC. TG testing kit, provided by Zhongsheng Beikong Biotechnology Co., Ltd.

3.2 Testing Grouping:

The tested objects are divided into five groups randomly with respect to the weight: I. Normal Control Group; II. Model Control Group; III. Water Extraction Group (namely the prepared products in the above mentioned example 11); IV. Alcohol Extraction Group (namely the prepared products in the above mentioned example 12); V. Supercritical Extraction Group (namely the prepared products in the above mentioned example 10). Each group contains 10 test subjects.

3.3 Testing Dosage

The sample is measured relative to the recommended dose for human, which is 10 g/60 kg/d, or 167 mg/kg/d. The dose given to the mice subjects is equivalent to 10 times the recommended dose for humans; it equates to 1670 mg/kg/d.

3.4 Medicine Delivery Method

First, reserpine injection was used to prepare spleen deficient and emaciated animal models. The mice were divided randomly into five groups: Normal Control Group, Emaciation Model Control Group, Water Extraction Group, Alcohol Extraction Group, and Supercritical Extraction Group. The Normal Control group and the Emaciation Model group were given basic feed on a daily basis, while the other groups were given daily basic feed and fed corresponding treatments orally. The data was statistically analyzed and the effects of the testing treatment relevant to the criteria observed. The testing period lasted 14 days.

4. Data Processing:

All the data is indicated in the format of the mean±standard deviation ($\bar{x}\pm s$) and the two groups of comparison adopts the t to test. Statistic analysis was undertaken using SPSS13.0 statistic analysis software; $p<0.05$ indicates the deviation is statistic significant.

5. Testing and the Results 5.1 Influence on the General Situation of the Mice

After five days of subcutaneous injection of reserpine, the mice showed symptoms such as weight loss, decreased food intake, decreased defecation, fluffy and dull hair, and lethargy. In each treatment group in which a test substance was applied, the aforementioned symptoms were observed to be relieved after the administration of drugs. The general situation of the weight and mental status of the supercritical extraction group showed the most significant recovery as compared with the Model Control group.

5.2 Effect on Weight of the Mice

The effects of each treatment on weight are shown in Table 1. From Table 1, we observed that the increase in weight in Water Extraction, Alcohol Extraction and Supercritical Extraction are evidently higher than that of the Model Control. Weight gain in the supercritical extraction group appears to be the most dramatic ($p<0.01$).

TABLE 1

Effect of treatment on the weight of the mice (unit: %).

| Group | mean ± SD | P |
|---|---|---|
| Normal control group | 32.75 ± 16.52 | |
| Model control group | 9.98 ± 5.31 | # |
| Water extraction testing group | 13.75 ± 4.57 | * |
| Alcohol extraction testing group | 14.12 ± 5.63 | * |
| Supercritical extraction testing group | 29.90 ± 4.18 | ** |

Note:
when comparing the normal control group to the model control group, "#" indicates $p<0.05$, "##" indicates $p<0.01$; when comparing the testing group to the model group, "NS" indicates $p>0.05$, "*" indicates $p<0.05$, "**" indicates $p<0.01$.
The legend is the same for the other tables below.

5.3 Effect on the Propulsion Rate of the Mice Intestine

Effects of each treatment on intestinal propulsion rate in the mice are shown in Table 2. From Table 2, we observed that intestinal propulsion rate in the mice in each treatment group appears lower than that of the model group. Of each treatment group, rate in the supercritical extraction group is the lowest with a significant difference from the control groups ($p<0.01$).

TABLE 2

The influence of each group of medicine to the mice small intestine's propulsion rate (unit: %)

| Group | mean ± SD | P |
|---|---|---|
| Normal control group | 67.93 ± 11.21 | |
| Model control group | 87.93 ± 9.17 | # |
| Water extraction testing group | 74.99 ± 8.29 | * |
| Alcohol extraction testing group | 74.12 ± 7.17 | * |
| Supercritical extraction testing group | 63.41 ± 8.58 | ** |

5.4 Effects on the Body to Fat Ratio.

Effects of each treatment on the body/fat ratio are shown in Table 3. From Table 3 we observed that mice body/fat ratio in each treatment group is higher than that of the model group. Of the treatment groups, supercritical extraction group is the highest, and is significantly different from the control group ($p<0.01$).

TABLE 3

Effects of treatment on mice body/fat ratio (unit: %)

| Group | mean ± SD | P |
|---|---|---|
| Normal control group | 0.457 ± 0.089 | |
| Model control group | 0.100 ± 0.069 | ## |
| Water extraction testing group | 0.195 ± 0.138 | NS |
| Alcohol extraction testing group | 0.249 ± 0.255 | * |
| Supercritical extraction testing group | 0.421 ± 0.197 | ** |

5.5 Effect on Mice Serum Content

Effects of each treatment on the contents of mice serum (namely gastrin, IL-2 and zinc) are shown in Table 4. From Table 4 we observed the following: 1) GAS is evidently higher in the treatment groups than that of the model group, 2) gastrin level in the mice serum of the Supercritical Extraction group is the highest and is significantly different when compared to the model group ($p<0.01$), 3) IL-2 level in the serum of treatment group is evidently higher than that of the model group, 4) IL-2 level in the Supercritical Extraction group is the highest compared to the model group, bears significant difference ($p<0.01$), 5) zinc level in each treatment group is higher than that in the model control group, 6) zinc level in the supercritical extraction group serum is the highest and significantly different from the model group ($p<0.01$).

TABLE 4

Mice serum gastrin, IL-2 and zinc

| Group | GAS(pg/ml) | mean ± SD<br>IL-2(ng/L) | Zn(mg/L) |
|---|---|---|---|
| Normal control group | 42.61 ± 25.72 | 12.14 ± 4.07 | 9.26 ± 0.47 |
| Model control group | 15.76 ± 23.57## | 6.97 ± 3.37# | 4.36 ± 0.43# |
| Water extraction testing group | 26.93 ± 17.38* | 10.31 ± 3.67* | 6.31 ± 0.36* |
| Alcohol extraction testing group | 30.66 ± 14.29* | 11.99 ± 2.41* | 7.01 ± 0.31* |
| Supercritical extraction testing group | 43.02 ± 15.15** | 14.93 ± 2.53** | 9.51 ± 0.48** |

5.6 Effects on Motilin in the Mice Serum

Effects of each treatment on motilin in mice serum are shown in Table 5. From Table 5 we observed that the motilin level in mice serum in each treatment group is notably lower than that of the model group; values in the supercritical group being the lowest and significantly different from the model control ($p<0.01$).

TABLE 5

Effects of treatments on motilin levels in mice serum(unit: pg/ml)

| Group | mean ± SD | P |
|---|---|---|
| Normal control group | 152.97 ± 24.85 | |
| Model control group | 223.69 ± 25.89 | ## |
| Water extraction testing group | 197.81 ± 23.37 | * |
| Alcohol extraction testing group | 183.26 ± 25.25 | * |
| Supercritical extraction testing group | 153.67 ± 27.61 | ** |

6. Summary

The tangerine peel extraction by means of water extraction, alcohol extraction, and supercritical extraction in this invention has notable effects in the weight gain on emaciated mice models produced by reserpine. Of the three extraction methods, supercritical extraction appears to be the most effective in restoring weight status.

What is claimed is:

1. A method of promoting weight gain in an underweight person who is spleen deficient and emaciated, comprising administering to said person a composition comprising an effective amount of a tangerine (*Citrus reticulata*) peel extract and an acceptable carrier, wherein the extract is prepared by extracting tangerine peels with supercritical $CO_2$.

2. The method according to claim 1 wherein the supercritical $CO_2$ extraction is performed at a flow rate of 1-100 L/h for 1-3 hours, under a pressure of between about 10 to 40 MPa and a temperature of between about 30 to 50° C.

3. The method according to claim 1, wherein the tangerine peel is broken into pieces of about 10-80 mesh prior to extracting, and wherein the tangerine peel extract is further concentrated and dried after extracting.

* * * * *